United States Patent [19]

Johnson

[11] Patent Number: 4,539,159

[45] Date of Patent: Sep. 3, 1985

[54] PROCESS FOR REACTION OF MERCAPTOPHENOLS WITH VINYL COMPOUNDS

[75] Inventor: Mark R. Johnson, Breckenridge, Mich.

[73] Assignee: The Dow Chemical Company, Midland, Mich.

[21] Appl. No.: 603,040

[22] Filed: Apr. 23, 1984

[51] Int. Cl.$^3$ .................. C07C 121/75; C07C 149/40
[52] U.S. Cl. ................................. 260/465 F; 560/17; 568/29; 568/41; 568/43
[58] Field of Search ...................... 260/465 F; 560/17; 568/29, 41, 42, 43

[56] References Cited

U.S. PATENT DOCUMENTS 4,012,523  3/1977  Wagner .
4,311,637  1/1982  Cottman .

FOREIGN PATENT DOCUMENTS 82810476.0  3/1983  European Pat. Off. .
49-75551    7/1974  Japan .

*Primary Examiner*—Dolph H. Torrence
*Attorney, Agent, or Firm*—Donald Corneglio

[57] ABSTRACT

An improved process for preparing derivatives of mercaptophenols containing nitrile, carbonyl, sulphone or ester groups characterized by reacting the components in a polar solvent with an amine catalyst. The catalyst can be removed from the product by co-distillation with the solvent to leave a relatively pure product free of contaminant without the need for further purification steps. The preferred amine catalysts are tertiary amines.

7 Claims, No Drawings

PROCESS FOR REACTION OF MERCAPTOPHENOLS WITH VINYL COMPOUNDS

BACKGROUND OF THE INVENTION

This invention generally relates to an improved process for preparing derivatives of mercaptophenols. Further, the invention provides for an improved process for preparing hindered phenol sulfides containing a nitrile, carbonyl, sulphone or ester group from the reaction of mercaptophenols with vinyl compounds containing a conjugated nitrile, carbonyl, sulphone or ester group.

The prior art generally teaches the preparation of mercaptophenol derivatives which are extremely useful as stabilizers for various organic and polymeric materials. A number of mercaptophenol derivatives are known to be useful as antioxidants and in pharmaceutical applications. In particular, Japanese Application No. 47-115575 discloses the preparation of mercaptophenol derivatives containing nitrile or carbonyl groups. European Patent Application No. 82810476.0 discloses mercaptophenols containing ester groups with improved stabilizer performance and U.S. Pat. No. 4,311,637 discloses polyphenolic esters of mercaptophenols useful as antioxidants.

The compounds disclosed by the prior art are generally produced by reacting the components in the presence of a proton acceptor. Typically, the proton acceptors are chosen from bases such as lithium salts, alkali metals, alkali and alkaline earth hydroxides, alkaline earth carbonates and tertiary amines. In addition, the reaction is generally carried out in non-polar solvents such as benzene, toluene and xylene or, alternatively without solvent. While such techniques are adequate to react the components, the processes suffer from slow reaction rates and, consequently produce by-products. In particular, the by-product disulfide is formed from the mercaptophenol due to the presence of traces of oxygen. Further, the predominant use of inorganic proton acceptors results in formation of salts which are not easily removed from the final product.

Japanese Patent Application No. 47-115575 discloses the use of non-polar solvents and polar solvents such as acetonitrile, dioxane, and pyridine; however, it requires the use of a suitable base such as alkali metal, alkali hydroxides and ammonium salts. The reaction times varied from 6 to 8 hours and the final product was recrystallized with n-hexane in order to purify the product.

Due to the difficulties and costs caused by slow reaction times and removal of by-products, it would be desirable to improve the process for preparation of mercaptophenol derivatives. Surprisingly, it has been discovered that by employing an amine base catalyst in a polar solvent the reaction between mercaptophenols and vinyl compounds containing nitrile, carbonyl, sulphone or ester groups proceeds rapidly to form the desired product with very little disulfide formation and; therefore, the product is of high purity. Further, the catalyst can be easily removed by co-distillation with the solvent.

SUMMARY OF THE INVENTION

The invention provides for an improved process for preparing derivatives of mercaptophenols containing nitrile, carbonyl, sulphone or ester groups by reacting a mercaptophenol with a vinyl compound containing a conjugated nitrile, carbonyl, sulphone or ester group. The process is characterized by reacting said mercaptophenol and said vinyl compound in a polar solvent with an amine catalyst. The process temperature is not critical and can be from 0° C. to about the reflux temperature of the polar solvent employed. The preferred amine catalyst is a tertiary amine.

Additionally, the process can include the step wherein the amine catalyst is removed by co-distillation with the polar solvent. The preferred polar solvent is acetonitrile and the preferred amine catalyst is triethyl amine.

Some advantages provided by the subject process are rapid formation of the desired product with very little formation of contaminants and ease of catalyst removal. Further, the product has a high degree of purity without additional purification steps.

DETAILED DESCRIPTION OF THE INVENTION

The improvement of the present invention relates to a process which generally comprises reacting mercaptophenols and vinyl compounds containing a nitrile, carbonyl, sulphone or ester groups as is well known in the art. The improvement comprises reacting the components in a polar solvent with an amine based catalyst. The use(s) of the compounds prepared from mercaptophenols and vinyl compounds containing a nitrile, carbonyl, sulphone or ester group is generally well known in the art and is taught in various publications disclosed herein.

Generally, the reaction of mercaptophenols with the vinyl compound can be structurally depicted as follows:

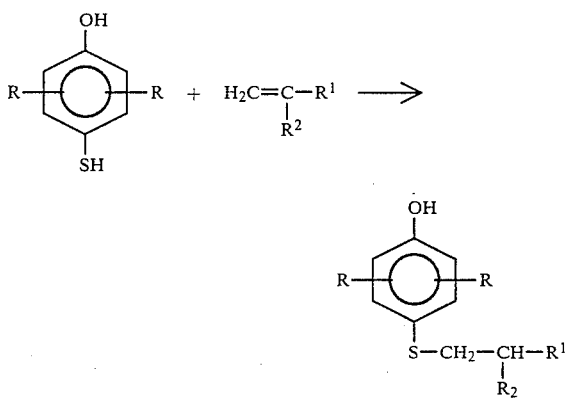

As shown above the R groups are independently a hydrogen, an alkyl group, an alkaryl group or a hydroxyaryl group, $R^1$ is a nitrile, carbonyl, sulphone or ester group and $R^2$ is a hydrogen or alkyl group.

With respect to the mercaptophenol compound, the preferred species comprises 2,6-di-t-butyl-4-mercaptophenol. Other suitable mercaptophenols are taught in U.S. Pat. Nos. 4,012,523 and 4,311,637 and European Patent Application No. 82810476.0.

With regard to the various vinyl compounds that can be employed, the acrylate esters such as methyl acrylate, maleic anhydride, 1,6-hexanediol diacrylate and reaction products of hydroxyethyl acrylate and isocyanatoalkyl methacrylate are preferred. The vinyl compounds can also comprise $\alpha,\beta$-unsaturated ketones, aldehydes, carboxylic anhydrides, nitriles and sulphones. Other suitable vinyl compounds containing conjugated nitrile, carbonyl, sulphone and ester groups are considered within the scope of this invention. Suitable vinyl compounds are those containing electron withdrawing groups. Vinyl compounds containing a conjugated carbonyl group can include $\alpha,\beta$-unsaturated ketones and aldehydes, and $\alpha,\beta$-unsaturated carboxylic anhydrides.

More generally, the reaction of mercaptophenols and vinyl compounds containing nitrile, carbonyl, sulphone and ester groups for the preparation of useful mercaptophenol derivatives is disclosed in U.S. Pat. Nos. 4,311,637 and 4,012,523, European Application No. 82810476.0 and Japanese Publication KOKAI No. 49-75551/1974.

The subject invention is characterized by reacting the various mercaptophenol and vinyl compounds taught above, in a polar solvent with an amine catalyst. When the reaction is carried out by the subject invention a product of high purity is rapidly formed with very little by-product, i.e., disulfide formation. Further the product does not contain difficult to remove catalyst or catalyst by-product as the amine catalyst can be removed by co-distillation with the solvent.

Generally, the polar solvents include those solvents which are polar in nature and are non-reactive solvents with the reaction components. Representative polar solvents which can be employed are acetonitrile, isopropanol, methanol, ethanol and the like. Methylene chloride can also be employed; however, it does not perform as well as other polar solvents. Therefore, polar solvents exhibiting polar characteristics greater than or equal to methylene chloride are preferred. The polar characteristic of a solvent can be easily predicted from standard tables of dielectric constants and polarity index. One such preferred polar solvent is acetonitrile.

With respect to the catalyst employed in the improved process, it has been found that the group of non-reactive amine catalysts perform especially well when dispersed in the polar solvent described above. What is meant by "non-reactive amine catalyst" is that the catalyst does not react with other components produced or present in the subject reaction such that the activity of the catalyst is impaired. The use of an amine catalyst is especially preferred due to its ease of removal from the final reaction product by distillation. Further, the amine catalyst is highly soluble in the polar solvent which contributes to its excellent activity and ability to be co-distilled from the final product. Preferably, the amine catalysts are non-reactive tertiary amines, of a base strength similar to triethylamine, trimethylamine and tributylamine. The most preferred amine catalyst is triethylamine.

The improved reaction of the subject invention generally proceeds under commonly employed reaction conditions for the particular reaction component. That is, the reaction can be conducted from about 0° C. to the reflux temperature of the polar solvent or particular reactants employed. Naturally, lower temperatures would detract from the improved reaction rate. More particularly, the reaction rate is dependent on various variables present in the system such as temperature, concentration of reactants and the mutual solubilities of the components.

The following example is provided to demonstrate the improved process of the invention.

EXAMPLE I

Reaction of 2,6-Di-t-butyl-4-mercaptophenol with Tetraethyleneglycol Diacrylate.

A solution of 1.84 g of tetraethyleneglycol diacrylate and 10.0 ml of nitrogen purged acetonitrile was treated with 2.9 g of 2,6-di-t-butyl-4-mercaptophenol and 0.2 ml of triethylamine catalyst. The reaction was carried out at ambient temperature with stirring and was completed in approximately one hour.

The solvent, acetonitrile, was removed under reduced pressure and a product of $\beta$-arylmercaptopropionate was collected. The $\beta$-arylmercaptopropionate was present as a thick oil with virtually no disulfide contaminant present.

EXAMPLE II

Reaction of 2,6-Di-t-butyl-4-mercaptophenol with Methyl Acrylate

A solution of 5.0 g (21.0 mmol.) of 2,6-di-t-butyl-4-mercaptophenol and 10 ml of acetonitrile was treated at room temperature with 1.81 g (21.0 mmol.) of methyl acrylate and 68 mg (0.67 mmol.) of triethylamine. The reaction mixture was stirred at ambient temperature for 1.5 hours and then the solvent was removed under reduced pressure to yield 6.8 g of the desired product—$\beta$-arylmercaptopropionate (m.p. 63°–64.5° C.). The yield was essentially 100 percent and the degree of purity was confirmed by the correspondence of the melting point of the product collected with that reported in the literature (m.p. 63°–64.5° C., lit. 62°–63.5° C.).

What is claimed is:

1. An improved process for preparing derivatives of mercaptophenols containing nitrile, carbonyl, sulphone or ester groups by reacting a mercaptophenol with a vinyl compound containing a conjugated nitrile, carbonyl, sulphone or ester group said process characterized by reacting said mercaptophenol and said vinyl compound in a polar solvent with an amine catalyst.

2. The process of claim 1 which is conducted at from about 0° C. to about the reflux temperature of said polar solvent.

3. The process of claim 1 wherein said amine catalyst is removed by co-distillation with said polar solvent.

4. The process of claim 1 wherein said polar solvent has a polar characteristic greater than or equal to methylene chloride.

5. The polar solvent of claim 4 which is acetonitrile.

6. The process of claim 1 wherein said amine catalyst is a tertiary amine catalyst.

7. The tertiary amine catalyst of claim 6 which is triethylamine.

* * * * *